(12) United States Patent
Smith

(10) Patent No.: US 9,795,682 B2
(45) Date of Patent: Oct. 24, 2017

(54) BEVERAGES WITH COMPOSITIONS OF VINEGAR

(71) Applicant: Louise M Smith, Henderson, NV (US)

(72) Inventor: Louise M Smith, Henderson, NV (US)

( * ) Notice: Subject to any disclaimer, the term of this patent is extended or adjusted under 35 U.S.C. 154(b) by 627 days.

(21) Appl. No.: 14/287,004

(22) Filed: May 24, 2014

(65) Prior Publication Data

US 2014/0255525 A1      Sep. 11, 2014

Related U.S. Application Data

(63) Continuation-in-part of application No. 13/987,806, filed on May 16, 2012, now abandoned.

(51) Int. Cl.
| | |
|---|---|
| *A61K 36/752* | (2006.01) |
| *A61K 35/64* | (2015.01) |
| *A61K 47/46* | (2006.01) |
| *A61K 36/889* | (2006.01) |
| *A61K 36/73* | (2006.01) |
| *A23L 2/02* | (2006.01) |
| *C12J 1/08* | (2006.01) |
| *A23L 33/105* | (2016.01) |
| *A61K 36/23* | (2006.01) |
| *A61K 35/644* | (2015.01) |
| *A61K 36/534* | (2006.01) |

(52) U.S. Cl.
CPC ............... *A61K 47/46* (2013.01); *A23L 2/02* (2013.01); *A23L 33/105* (2016.08); *A61K 36/73* (2013.01); *A61K 36/889* (2013.01); *C12J 1/08* (2013.01); *A61K 35/644* (2013.01); *A61K 36/23* (2013.01); *A61K 36/534* (2013.01); *A61K 36/752* (2013.01)

(58) Field of Classification Search
CPC .................................................. A61K 36/752
See application file for complete search history.

(56) References Cited

U.S. PATENT DOCUMENTS

| | | | |
|---|---|---|---|
| 3,958,023 A | 5/1976 | Butterworth | |
| 5,356,641 A | 10/1994 | Bowen | |
| 5,811,147 A | 9/1998 | Yamada | |
| 5,882,706 A | 3/1999 | Kawashima | |
| 6,694,985 B1 | 2/2004 | Kim | |
| 6,841,187 B2 | 1/2005 | Sumihara | |
| 6,932,988 B2 | 8/2005 | Cruse | |
| 7,005,149 B2 | 2/2006 | Kato | |
| 2003/0096049 A1 | 5/2003 | Sumihara | |
| 2005/0276884 A1* | 12/2005 | Schydlowsky | G06Q 20/20 426/106 |
| 2009/0053361 A1* | 2/2009 | Pipko | C12J 1/00 426/17 |
| 2009/0196973 A1* | 8/2009 | Piatko | A23C 11/08 426/565 |
| 2010/0092622 A1 | 4/2010 | Warner | |
| 2010/0216098 A1* | 8/2010 | Montgomery | G09B 19/0092 434/127 |
| 2010/0317562 A1* | 12/2010 | Paolella | A23D 7/0053 514/1.1 |
| 2011/0318468 A1 | 12/2011 | Kakhaberi | |
| 2012/0177799 A1 | 7/2012 | Nagel | |
| 2014/0087053 A1 | 3/2014 | Ferrari | |
| 2014/0190496 A1* | 7/2014 | Wensley | A24F 47/008 131/273 |

\* cited by examiner

*Primary Examiner* — Chris R Tate
(74) *Attorney, Agent, or Firm* — IDP Patent Services; Olay M. Underdal

(57) ABSTRACT

A composite vinegar infused juice blend includes juice blend, including natural fruit and/or vegetable juices; and vinegar composition, including coconut vinegar; and apple cider vinegar. A beetroot based juice blend includes beet juice, carrot juice, apple juice, and water, with equal parts of coconut vinegar and apple cider vinegar. Orange and carrot, mango and sweet potato based juice blends are disclosed. A sweet composite vinegar infused beverage for alleviation or treatment of flu or cold symptoms includes apple cider vinegar, coconut vinegar, water, organic honey, and peppermint extract. Also disclosed is a method for alleviation or treatment of flu or cold symptoms.

10 Claims, No Drawings

BEVERAGES WITH COMPOSITIONS OF VINEGAR

CROSS-REFERENCE TO RELATED APPLICATIONS

This application is a continuation-in-part of U.S. Non-Provisional application Ser. No. 13/987,806, filed May 16, 2012

FIELD OF THE INVENTION

The present invention relates generally to the field of dietary and health related beverages, and more particularly to such beverages with novel composition of vinegars.

BACKGROUND OF THE INVENTION

Health related beverages have become popular during the last decades. Often such beverages may contain various kind of fruit juices and blends.

Some related examples of vegetables and fruits that can be consumed as a juice or juice blend are:

I. Beetroots—Also called beets, they promote healthy blood circulation, and the high content of iron in beets regenerates and reactivates the red blood cells and supplies fresh oxygen to the body. The copper content in beets helps make the iron more available to the body. The human body converts nitrates in beets to nitric oxide, which may play a role in helping to support exercise endurance and recovery. Beets contain vitamin A, & C, Thiamine (B1), Riboflavin (B2), Niacin (B3), pyridoxine (B6), Calcium, Iron, Phosphorus, Fat, Carbohydrates, Protein, Manganese sodium, potassium, Fiber, Betaine, Alkaline Enzymes, Folic Acid, and Betacyanin.

II. Carrots—Contain beta-carotene and other carotenes. Carrots also have a very strong antioxidant activity and may aid in immune system support. In addition, they may aid and support mucous membrane, skin and eye health. They also are a ready source of energy and may aid to reduce the risk of heart disease, as well as calm the bowel and slow down bacterial development.

III. Mango—Mango juice is an excellent natural source of vitamins, microelements and nutrients. This tropical fruit is very rich in potassium, one of the most important microelements for our cardiovascular health. One small mango provides 25% of daily allowance (RDA) for vitamin C, 67% of RDA for vitamin A, and a large amount of Vitamin E & K. In addition, mango is rich in phosphorus, potassium, and magnesium.

Mango fruit is also rich in pre-biotic dietary fiber, vitamins, minerals, poly-phenolic flavonoids, antioxidants and phytonutrients compounds. Several trial studies suggest that poly-phenolic antioxidant compounds in mango offer some degree of protection against heart and colon cancers. Similarly, scientists have identified a strong link between fiber consumption and a lower risk of cancers of the gastrointestinal tract.

Lupeol, a triterpene present in mango, has been shown to possess anti-cancer properties. The phenols in mangoes, such as quercetin, isoquercitrin, astragalin, fisetin, gallic acid and methylagallat, as well as the abundant enzymes, have cancer-preventing capacities. Mango is also high in a soluble dietary fiber known as pectin Vinegar has historically been recognized as having a number of health benefits. Limited trials in rodents have indicated cholesterol lowering and lowering of blood pressure. Prior to discovery of modern hypoglycemic agents, diabetics used vinegar teas to control symptoms. A number of medical studies have shown reduction of the glycemic index for carbohydrate foods. Vinegar was thought to be useful for treating infections in historic times. It is known that the active ingredient in vinegar, acetic acid is effective against mycobacteria, including drug-resistant strains.

Vinegar has historically had limited use in beverages, due to an association of bad taste of beverages with traditional vinegar compositions. The shrub was a popular cocktail or soft drink that was popular during America's colonial era. It is made by mixing a vinegared syrup with spirits, water, or carbonated water. A main constituent is a sweetened vinegar-based syrup, also known as drinking vinegar. Thus, in these drinks the traditional vinegar taste is masked with a high content of sugar, thereby making the drinks potentially unhealthy, even when combined with healthy ingredients.

As such, considering the foregoing, it may be appreciated that there continues to be a need for novel and improved devices and methods for beverages containing juice from fruits and vegetables, together with vinegar.

SUMMARY OF THE INVENTION

The foregoing needs are met, to a great extent, by the present invention, wherein in aspects of this invention, enhancements are provided to the existing model of beverages with vinegar.

In aspects of this invention, a fruit and/or vegetable juice beverage with novel compositions of vinegar, referred to as a composite vinegar infused juice blend, is based on novel compositions of raw juice blends with compositions of vinegar. In related aspects, these beverages are 100% organic, raw, and natural, without the use of chemical preservatives, such that they may be used as part of a healthy living lifestyle and diet.

In related aspects, vinegar acts as a natural preservative. When combined with raw fruit and vegetable juices, the vinegar kills unhealthy bacteria. A proper amount of vinegar will produce probiotics. A suitable range for vinegar in beverages is 30-40% by volume, as less than 30% percent will not destroy the unhealthy bacteria, and more that 40% percent will alter the taste in an undesirable manner. The proper amount of vinegar may produce probiotics.

In aspects of this invention, fruit beverages with compositions of vinegar are enhanced with components, such as vitamins, minerals enzymes, phytonutrients, and probiotics that may provide a range of health benefits, including improving the health of the digestive system.

Aspects of this invention describe a novel combination of raw coconut vinegar and raw mother of apple cider vinegar, which is composed together with specific blends of juices of fruits and vegetables.

In related aspects, the vinegar composition gives beverages a longer shelf life while preserving the potency and freshness of its raw juice ingredients. The novel combination of raw coconut vinegar and raw mother of apple cider vinegar provides a unique and flavorful taste in combination with certain raw juice blends, such that the resulting combined taste sensation is pleasant to a majority of human consumers, while allowing for a higher concentration of active ingredients of the constituent vinegars, including a higher concentration of acetic acid. In related aspects, this unique vinegar composition provides a pleasant taste without requiring the addition of large amounts of sugar.

In related aspects, the combined vinegar juice blend is a raw, organic, and natural substance in a liquid form, which allows the body to absorb it quickly into the blood stream, such that it is distributed rapidly to the cells of the body. The digestive system does not have to break it down in order to absorb the ingredients of the composite vinegar infused juice blends.

In related aspects, the combined vinegar juice blend may have a favorable effect on both the bowel function and cholesterol levels, and further may have a protective function against colon cancer due to the combination of beta-cyanin and fiber content. Along with combinations of special vegetable roots, fruits and exotic unheated enzymatically live vinegars, the combined vinegar juice blend contain prebiotic fibers, a natural, non-digestible food ingredients, which promotes helpful bacteria and other microorganisms in in the intestines. The vinegars add naturally occurring organic acids that provide the body with important minerals such as potassium, calcium, sodium and magnesium. These and other minerals form compounds in the body that convert acid body fluids into alkaline.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

N/A

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Throughout this disclosure, a juice shall be understood to mean a liquid that is naturally contained in or derived from fruit or vegetables. It can also refer to liquids that are flavored with these or other biological food sources such as meat and seafood.

Throughout this disclosure, a juice blend shall be understood to mean a mixture of one or more individual juices. As an example, pure orange juice is a juice blend, and a mixture of orange juice, apple juice, and tomato juice is a juice blend.

Throughout this disclosure, a raw juice shall be understood to mean a juice, which has not undergone any heating, pasteurization, concentration, distillation, or other processing, other than extracting the raw juice from a juice source, such as a vegetable, a fruit, or other biological food item that contains a liquid.

In an embodiment, a composite vinegar infused juice blend can comprise
    a. A juice blend, comprising a blend of natural fruit and/or vegetable, or other juices; and
    b. A vinegar composition, further comprising:
        i. A coconut vinegar; and
        ii. An apple cider vinegar.

In a related embodiment, the vinegar composition can comprise substantially equal parts of the coconut vinegar and the apple cider vinegar, such that the overall percentage of volume for the vinegar composition is 30-40% of the composite vinegar infused juice blend.

In a related embodiment, the vinegar composition can contain acetic acid in a range of 4-8 percent by weight.

In a related embodiment, the vinegar composition can further comprise mother of vinegar. In a further related embodiment, the mother of vinegar can be comprised of individual pieces of mother of vinegar such that each piece has a volume in a range 5-25 cubic mm, whereby the composite vinegar infused juice blend can be more pleasant to drink.

In a related embodiment a beet based composite vinegar infused juice blend, can comprise in total percentages by weight:
    a. A juice blend, further comprising:

| | | |
|---|---|---|
| i. | Beet Juice | 24% |
| ii. | Carrot Juice | 16% |
| iii. | Apple juice | 12% |
| iv. | Water | 12% | b. A vinegar composition, further comprising:

| | | |
|---|---|---|
| i. | Coconut Vinegar | 18% |
| ii. | Apple Cider Vinegar | 18 oz |

In a further related embodiment of the beet based composite vinegar infused juice blend, the water can be filtered water, such as water filtered via reverse-osmosis filtration.

In a related embodiment, an orange-carrot based composite vinegar infused juice blend, can comprise in total percentages by weight:
    a. A juice blend, further comprising:

| | | |
|---|---|---|
| i. | Carrot Juice | 36% |
| ii. | Orange Juice | 24% |
| iii. | Water | 10% | b. A vinegar composition, further comprising:

| i. | Coconut Vinegar | 15% |
|---|---|---|
| ii. | Apple Cider Vinegar | 15% |

In a related embodiment, a mango-orange based composite vinegar infused juice blend, can comprise in total percentages by weight:
a. A juice blend, further comprising:

| i. | Mango Juice | 36% |
|---|---|---|
| ii. | Orange Juice | 24% |
| iii. | Water | 10% | b. A vinegar composition, further comprising:

| i. | Coconut Vinegar | 15% |
|---|---|---|
| ii. | Apple Cider Vinegar | 15% |

In a related embodiment, a sweet potato based composite vinegar infused juice blend, can comprise in total percentages by weight:
a. A juice blend, further comprising:

| i. | Sweet Potato Juice | 27% |
|---|---|---|
| ii. | Carrot Juice | 18% |
| iii. | Apple Juice | 14% | b. A vinegar composition, further comprising:

| i. | Coconut Vinegar | 20.5% |
|---|---|---|
| ii. | Apple Cider Vinegar | 20.5% |

In an embodiment, a sweet composite vinegar infused beverage for alleviation or treatment of flu or cold symptoms, can comprise:

| a. | Apple Cider Vinegar | 4 oz. | (23.5%) |
|---|---|---|---|
| b. | Coconut vinegar | 4 oz. | (23.5%) |
| c. | Distilled Water | 8 oz. | (47%) |
| d. | Organic honey | 1 Tbsp. | (4.4%) |
| e. | Peppermint Extract | 8 ml. | (1.6%) |

Percentages in parenthesis indicate relative proportions by weight.

In a further related embodiment, a sweet composite vinegar infused beverage for alleviation or treatment of flu or cold symptoms, can comprise:

| a. | Apple Cider Vinegar | 4 oz. | (23.5%) |
|---|---|---|---|
| b. | Coconut vinegar | 4 oz. | (23.5%) |
| c. | Lemon juice | 4 oz. | (23.5%) |
| d. | Distilled Water | 4 oz. | (23.5%) |
| e. | Organic honey | 1 Tbsp. | (4.4%) |
| f. | Peppermint Extract | 8 ml. | (1.6%) |

In a related embodiment, the sweet composite vinegar infused beverage can upon ingestion by a patient alleviate flu and cold symptoms, and open up the respiratory track, thereby providing a quick relief to the patient. The sweet composite vinegar infused beverage functions as a natural antiviral remedy, exhibiting a golden color, and a sour/tangy sweet taste. It may help loosen mucus in the lungs and boost the body's defense when consumed while warm.

In a related embodiment, a therapeutically effective amount of the sweet composite vinegar infused beverage can be an amount of 0.25-1.0 cups.

In various related embodiments, the apple cider and coconut vinegars may help reduce swollen tissue and fight fungal, bacterial and viral infections. The vinegar composition with honey provides a pleasant flavor and taste. The honey also possesses antiseptic and antibacterial properties. Peppermint also helps with the respiratory system, including for coughs, and cold. It may also inhibit histamine release. Additionally, the peppermint is an expectorant and decongestant, and may help clear the respiratory tract.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:
1. A composite vinegar infused juice blend for alleviating symptoms of the flu and/or the common cold comprising effective amounts of:
    i. lemon juice;
    ii. water;
    iii. honey;
    iv. peppermint extract; and
    v. a vinegar blend,
    wherein the vinegar blend comprises substantially equal parts of a coconut vinegar and an apple cider vinegar, wherein the apple cider vinegar comprises apple cider mother of vinegar, and wherein the apple cider mother of vinegar is comprised of individual pieces thereof, such that each piece has a volume in a range of 5-25 cubic mm.
2. The composite vinegar infused juice blend of claim 1, wherein the coconut cider vinegar comprises coconut cider mother of vinegar.
3. The composite vinegar infused juice blend of claim 1, wherein the vinegar blend contains acetic acid in a range of 4-8% by weight.
4. A method for alleviating symptoms of the flu and/or the common cold in a human in need thereof, comprising administering to said human an effective amount of the composite vinegar infused juice blend according to claim 1.
5. A composite vinegar infused juice blend comprising:
    i. lemon juice, in a proportion of substantially 23.5% by weight;
    ii. water, in a proportion of substantially 23.5% by weight;
    iii. honey, in a proportion of substantially 4.4% by weight;
    iv. peppermint extract, in a proportion of substantially 1.6%, by weight; and
    v. a vinegar blend, in a proportion of substantially 47% by weight,
    wherein,
    the vinegar blend comprises substantially equal parts of a coconut vinegar and an apple cider vinegar.

6. The composite vinegar infused juice blend of claim 5, wherein the apple cider vinegar comprises apple cider mother of vinegar.

7. The composite vinegar infused juice blend of claim 6, wherein the apple cider mother of vinegar is comprised of individual pieces of apple cider mother of vinegar, such that each piece has a volume in a range of 5-25 cubic mm.

8. The composite vinegar infused juice blend of claim 5, wherein the coconut cider vinegar comprises coconut cider mother of vinegar.

9. The composite vinegar infused juice blend of claim 5, wherein the vinegar blend contains acetic acid in a range of 4-8% by weight.

10. A method for alleviating symptoms of the flu and/or the common cold in a human in need thereof, comprising administering to said human an effective amount of the composite vinegar infused juice blend according to claim 5.

\* \* \* \* \*